United States Patent [19]

Tsuji

[11] Patent Number: 4,548,550
[45] Date of Patent: Oct. 22, 1985

[54] METHOD AND SYSTEM FOR DRIVING BLOOD PUMPING DEVICES

[75] Inventor: Takashi Tsuji, Fujisawa, Japan

[73] Assignee: Nippon Zeon Co., Ltd., Tokyo, Japan

[21] Appl. No.: 609,084

[22] Filed: May 11, 1984

[30] Foreign Application Priority Data

May 11, 1983 [JP] Japan ................ 58-080686
May 11, 1983 [JP] Japan ................ 58-080687
May 11, 1983 [JP] Japan ................ 58-080688

[51] Int. Cl.[4] .................................... F04B 43/06
[52] U.S. Cl. .................................... 417/390; 417/394; 91/31; 604/153
[58] Field of Search ............... 417/390, 392, 394, 395, 417/478; 91/31, 6; 604/151, 153

[56] References Cited

U.S. PATENT DOCUMENTS

3,208,448 9/1965 Woodward ............ 417/395 X
3,955,557 5/1976 Takagi ............ 417/394 X
4,116,589 9/1978 Rishton ............ 417/394 X Primary Examiner—Leonard E. Smith
Attorney, Agent, or Firm—Armstrong, Nikaido, Marmelstein & Kubovcik

[57] ABSTRACT

A method and system for pneumatically driving a pump for an artificial heart is disclosed which can pump blood as approximate as possible to the natural heart without increasing the capacity of any pressure tank. A compensation drive pressure which compensates for the drop of the drive pressure is additionally applied to the pump whenever the drive pressure is applied to the pump.

8 Claims, 22 Drawing Figures

METHOD AND SYSTEM FOR DRIVING BLOOD PUMPING DEVICES

BACKGROUND OF THE INVENTION

The present invention relates to a driving system for pneumatically driven type pumps such as a blood pumping device and the like.

Figure 1:
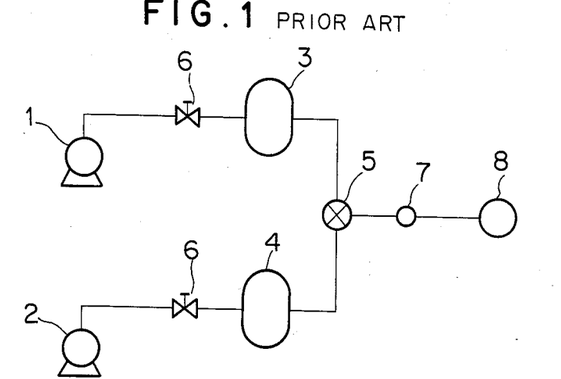
FIG. 1 is a block diagram of a conventional driving system.

As a driving system of this type there has been known, for example, a driving system of such a construction as shown in FIG. 1, in which indicated at numeral 1 is a compressor, at 2 a vacuum pump, at 3 a positive pressure tank, at 4 a negative pressure tank, at 5 an electromagnetic change-over valve and at 6 a pressure reducing valve.

The interior of the positive pressure tank 3 is maintained at a predetermined positive pressure by means of the compressor, while the interior of the negative pressure tank 4 is maintained at a negative pressure by the vaccum pump 2. Positive and negative pressures alternately act on (pressurize and suck in) and drive a pneumatically driven pump 8 such as a blood pumping device provided at a driving pressure outlet 7 from the positive pressure tank 3 and negative pressure tank 4 through the electromagnetic change-over valve 5.

According to the above driving system, in order to operate the pneumatically driven type pump 8 as per the rating by supplying predetermined pressures thereto, it is necessary that the capacity of the positive pressure tank 3 and that of the negative pressure tank 4 be set at a value, for example, several ten times (40-50 times) as large as that of the pneumatically driven type pump 8. This is for the following reason.

When the positive pressure tank 3 is opened by the electromagnetic change-over valve 5, the pressure in the tank 3 drops, while when the negative pressure tank 4 is opened, the pressure in this tank 4 rises. These pressure drop and rise are negligible if the capacities of the tanks are sufficiently large. However, if the tank capacities are not sufficient, the ratios of such pressure drop and rise are large. Since the response speed of the pressure reducing valve 6 is generally not so high, the valve 6 cannot immediately compensate for such pressure drop and rise, so that the pressure waveform at the driving pressure outlet 7 and that at the pneumatically driven type pump 8 are influenced by such pressure drop and rise. The solid line A in FIG. 2 shows a pressure waveform influenced by the pressure drop.

Figure 2:
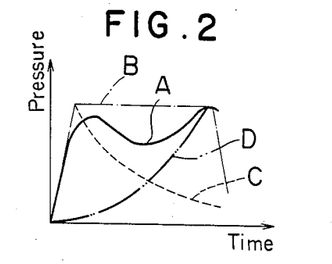
FIGS. 2 and 3 are pressure waveform diagrams reflecting the influence of pressure drop.

In FIG. 2, the alternate long and short dash line B represents an ideal waveform free from pressure drop, the dotted line C represents a pressure curve in the positive pressure tank 3 in the case of gas being not replenished, and the alternate long and two short dashes line D represents a pressure curve under operation of the pressure reducing valve 6.

Figure 3:
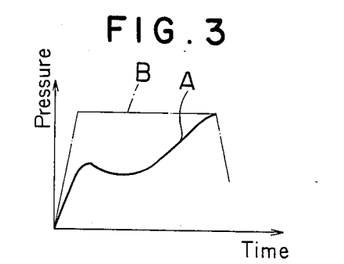

In the case where the flow path between the driving pressure outlet 7 and the pneumatically driven type pump 8 is long and is formed by a flexible hose of a small diameter, the pressure waveform in the pneumatically driven type pump 8 is influenced by the intratube pressure and tube deformation in addition to the pressure drop and is as if it had been passed through a low-pass filter as shown in FIG. 3.

Particularly in a blood pumping device, it is necessary that the blood pressure curve exhibited by the blood pump be as approximate as possible to that of a natural heart and, most ideally, identical with the latter. To this end, in driving systems for blood pumping devices, the foregoing pressure drop and rise must be kept to a minimum, so it is necessary that the capacities of the tanks 3 and 4 be set sufficiently large.

Thus, because of the necessity of making the capacities of the tanks 3 and 4 sufficiently large, the greater part of the driving system is occupied by the tanks 3 and 4, that is, it is difficult to attain reduction of size.

SUMMARY OF THE INVENTION

It is therefore an object of the present invention to provide a novel method and system for driving a blood pumping devices.

It is another object of the present invention to provide a system which is free of the difficulties encountered by the prior arts.

It is a further object of the present invention to provide a method and system for driving a blood pump so that the pump can pump blood having a changes in pressure as approximate as possible to that in the human body.

It is a further object of the present invention to provide a system for driving a pneumatically driven type pump, capable of operating the pump as per the rating and attaining reduction in size of the entire system through reduction of tank capacity.

In accordance with the present invention there is provided a driving method for a blood pumping device which is driven either by applying to a driving portion of a blood pumping device a positive pressure intermittently from a positive pressure tank connected through a pressure regulating valve to a high pressure source or by applying thereto positive and negative pressures alternatively from the said positive pressure tank and a negative pressure tank connected through a pressure regulating valve to a negative pressure source, comprising when the positive pressure or both the positive and negative pressures are exerted on the above driving portion, compensating pressures for pressure drop and rise in the positive and negative pressure tanks are exerted thereon in synchronism therewith without going through the pressure regulating valves.

In accordance with the present invention there is also provided a system for driving a type pump which is pneumatically driven by being alternatively applied with positive and negative pressures comprising a positive pressure source for producing said positive pressure, a positive pressure tank for accumulating the high pressure generated by the positive pressure source; said positive pressure tank being connected with the positive pressure tank, a positive pressure regulating valve between the positive pressure source and the positive pressure tank for regulating the pressure from the positive pressure source into a given pressure, a negative pressure source for producing a negative pressure, a negative pressure tank for accumulating the positive pressure generated by the negative pressure source, said negative pressure tank being connected with the negative pressure source, a negative regulating valve between the negative pressure source and the negative pressure tank for regulating the pressure from the negative pressure source into a given pressure, a change-over valve for alternatively connecting the positive and negative pressure tanks with an port which is to be connected with the pump, a positive pressure branch having an inlet between the positive pressure source and the positive pressuer regulator and an outlet between the positive pressure regulator and the pump for applying a pressure higher than that from the positive tank when the latter is applied upon the pump, and a negative pressure branch having an inlet between the negative pressure source and the negative pressure regulator and an outlet between the negative pressure regulator and the pump for applying a pressure lower than that from the negative pressure tank when the latter is applied upon the pump. Preferably the outlets of the positive and negative pressure branches are connected to the outlet of the system. Preferably the outlets of the positive and negative pressure branches are connected to the positive and negative pressure tank respectively. The negative and positive pressure branch may have sub-pressure tanks respectively.

BRIEF DESCRIPTION OF THE DRAWINGS

FIGS. 6(a), (b) and (c) are time charts of an electromagnetic change-over valve 5 and solenoid valves 14 and 16;

FIGS. 12(a)-(e) are time charts of an electromagnetic change-over valve 5 and solenoid valves 13a, 14, 15a and 16;

DETAILED DESCRIPTION OF THE EMBODIMENTS

The embodiments of the present invention will be described with reference to the drawings. For ease of understanding of the present invention a pneumatically driven pump 8 shown in FIG. 4 which is driven by a driver system of the present invention will now be described prior to the description of the driver system.

Figure 4:
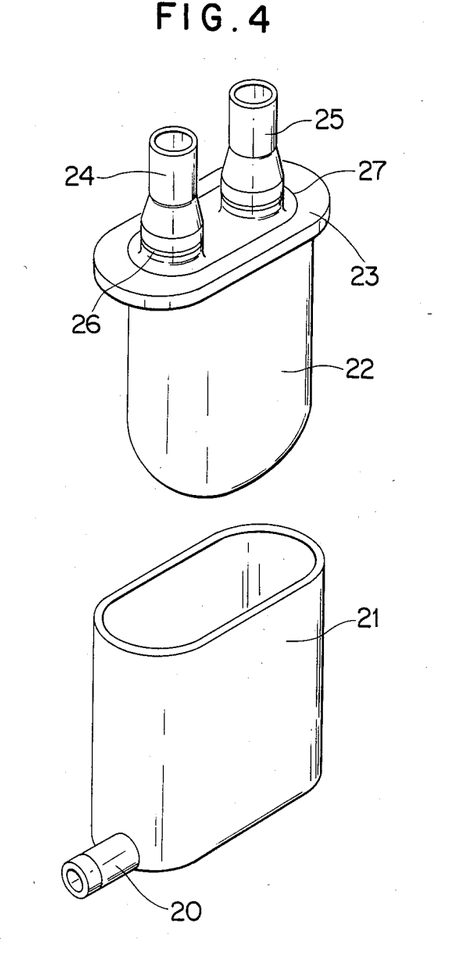
FIG. 4 is an exploded perspective view showing an example of a blood pumping device.

Referring now to FIG. 4, there is shown a pneumatically driven type pump 8 which is used as a pumping device for artificial heart. This pumping device is constructed, for example, as shown in FIG. 4, that is, a flat bag-like blood chamber 22 is enclosed in a pressure-resistant housing outer case 21 hermetically through a flange portion 23 formed at its upper portion, the case 21 having a gas introducing and discharging port 20. On the flange portion 23 are erected a blood introducing conduit 24 and a blood discharging conduit 25 substantially in parallel with each other, in which are mounted check valves 26 and 27, respectively.

The port 20 is connected to the driving pressure outlet 7, and when pressurized gas is introduced into the housing outer case 21, the blood chamber 22 is squeezed and crushed by the pressure of the gas and the blood therein is forced out from the blood discharging conduit 25 through the check valve 27. Then, when the pressure in the housing outer case 1 is reduced, the blood chamber 22 expands by virtue of its elastic restoring force and the check valve 26 opens, allowing blood to be introduced into the blood chamber 22 through the blood introducing conduit 24. By repeating these operations successively, blood is delivered periodically.

Figure 5:
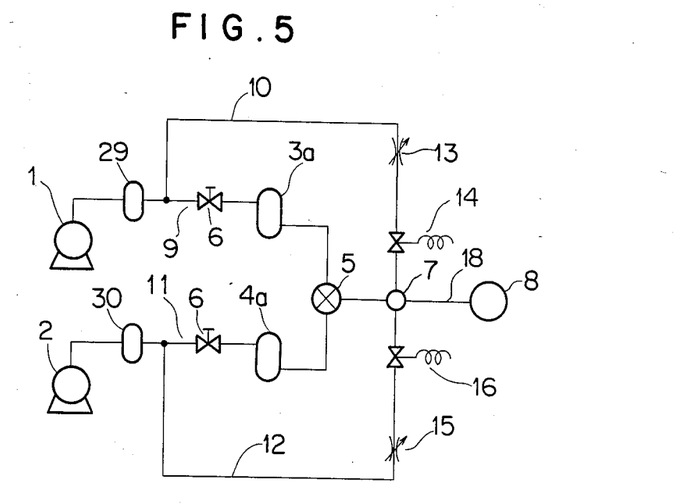
FIG. 5 is a block diagram showing an embodiment of the present invention.

Referring now to FIG. 5, there is shown an embodiment of the driving system of the present invention, in which the portions common to FIG. 1 are indicated at the same reference numerals. Explanation of such common portions will be omitted.

In this embodiment, from a positive pressure line 9 comprising a compressor 1, a positive pressure tank 3a, an electromagnetic chang-over valve 5 and a driving pressure outlet 7, there branches a branch line 10 which extends from between a pressure reducing valve 6 provided on the inlet side of the positive pressure tank 3a and the compressor 1 and is connected to the driving pressure outlet 7 thereby connecting the compressor 1 directly with the driving pressure outlet 7. Also from a negative pressure line 11 comprising a vacuum pump 2, a negative pressure tank 4a, the electromagnetic change-over valve 5 and the driving pressure outlet 7, there branches a branch line 12 which extends from between a pressure reducing valve 6 provided on the inlet side of the negative pressure tank 4a and the vacuum pump 2 and is connected to the driving pressure outlet 7 thereby connecting the vacuum pump 2 directly with the driving pressure outlet 7.

In the branch line 10 are mounted a control valve 13 and a solenoid valve 14, and also in the branch line 11 are mounted a control valve 15 and a solenoid valve 16.

Figure 6:
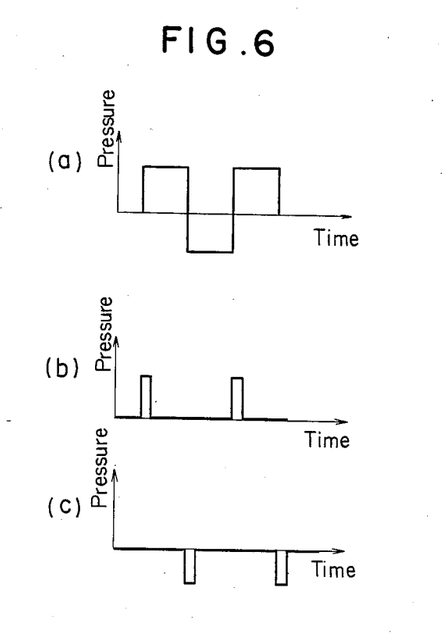

The solenoid valves 14 and 16 are each operated in synchronism with the electromagnetic change-over valve 5 by means of a control unit (not shown). FIG. 6 shows time charts of the solenoid valves 14 and 16 and electromagnetic change-over valve 5. According to the same figure, when the electromagnetic change-over valve 5 switches to the positive pressure tank 3a side, the solenoid valve 14 opens for a short time in synchronism therewith [FIG. 6(b)], while when the electromagnetic change-over valve 5 switches to the negative pressure tank 4a side, the solenoid valve 16 opens for a short tiem in synchronixm therewith [FIG. 6(c)].

Thus, in this embodiment, when positive and negative pressures are exerted on the pneumatically driven type pump 8 from the positive pressure tank 3a and negative pressure tank 4a upon operation of the solenoid valves 14 and 16 in synchronism with the solenoid valve 5, positive and negative pressures are exerted on the pump 8 also from the compressor 1 and vacuum pump 2 directly through the branch lines 10 and 12 in synchronism therewith to eliminate the influence of increase and decrease of pressure. The positive pressure from the branch line 10 is higher than the pressure in the positive pressure tank 3a and the negative pressure from the branch line 12 is lower than the pressure in the negative pressure tank 4a.

Figure 7:
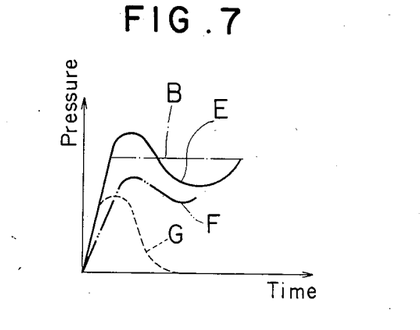
FIGS. 7 and 8 are pressure waveform diagrams obtained in the use of the driving system of the invention.
Figure 8:
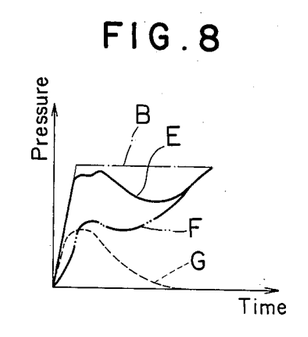

FIGS. 7 and 8 show pressure waveforms at the driving pressure outlet 7 and the pneumatically driven type pump 8 under action of positive pressure (under supply of pressurized gas). According to those figures, with only the positive pressure tank 3a, a predetermined pressure is not reached until response of the pressure reducing valve 6 due to the influence of pressure drop as shown in the alternate long and two short dashes line F, but pressurized gas is exerted on the pump directly from the compressor 1 through the branch line 10 by the solenoid valve 14 which opens for a short time in synchronism with the electromagnetic change-over valve 5 (see the dotted line G), thereby compensating for the pressure drop at the beginning of supply of the positive pressure, so that pressure waveform at the driving pressure outlet 7 and the pump 8 somewhat approaches the ideal waveform B as shown in the solid line E. The alternate long and two short dashes line F in Fig. 7 corresponds to the solid line A shown in FIG. 2, and the like line F in FIG. 8 corresponds to the solid line A shown in FIG. 3.

Consequently, it becomes possible to operate the pneumatically driven type pump as per the rating without setting large the capacity of the positive pressure tank 3a and that of the negative pressure tank 4a as previoulsy noted.

The amount of gas from the solenoid valves 14 and 16 can be adjusted by changing the valve port diameter of the solenoid valves 14 and 16, the length of flow path, or the opening of the control valves 13 and 15. If a flow path 18 (a flexible hose) from the driving pressure outlet 7 to the pneumatically driven type pump 8 is set at a predetermined constant length, the amount of gas can be adjusted by changing the valve port diameter of the solenoid valves 14 and 16, and in this case the control valves 13 and 15 are not needed.

The numerals 29 and 30 in FIG. 5 denote tanks respectively mounted in the positive pressure line 9 and negative pressure line 11, which tanks are for storing the pressures of the compressor 1 and vacuum pump 2, respectively.

Operation of the above embodiment will be described below.

The interior of the positive pressure tank 3a is maintained at a predetermined positive pressure by the compressor 1 and the interior of the negative pressure tank 4a is maintained at a predetermined negative pressure by the vacuum pump 2. When the electromagnetic change-over valve 5 switches to the positive pressure tank 3a side. Pressurized gas is fed from the valve 5 into the housing outer case 21 through the driving pressure outlet 7 and further through the port 20. At this time, the solenoid valve 14 opens in synchronism with the electromagnetic change-over valve 5 and pressurized gas is fed directly from the compressor 1 into the housing outer case 21 through the port 20 for a short time. Therefore, even if there occurs a pressure drop in the positive pressure tank 3a at the beginning of supply of the pressurized gas, the pressure waveform in the housing outer case 21 is not influenced at all. Consequently, the interior of the housing outer case 21 is pressurized up to a predetermined level without delay in rise, whereby the blood in the blood chamber 22 is forced out from the blood discharging conduit 25 through the check valve 27.

Then, when the electromagnetic change-over valve 5 switches to the negative pressure tank 4a side, the gas in the housing outer case 21 is sucked into the negative pressure tank 4a through the port 20 and then discharged to the exterior from the negative pressure tank 4a through the pressure reducing valve 6 by means of the vacuum pump 2. At this time, the solenoid valve 16 opens in synchronism with the electromagnetic change-over valve 5 and a suction of gas is effected directly from the interior of the housing outer case 21 by means of the vacuum pump 2. Therefore, there occurs an increase of pressure in the negative pressure tank 4a at the beginning of the suction of gas and the pressure in the housing outer case 21 is reduced to a predetermined level without delay in fall, whereby the check valve 26 is opened (while the check valve 27 is kept closed) and blood is introduced into the blood chamber 22 through the blood introducing conduit 24.

Thus, the blood pumping device can be operated as per the rating and it becomes possible to make the blood pressure curve exhibited by the blood pumping device as approximate as possible to that of a natural heart.

Although in the above embodiment the driving system of the present invention was applied to the blood pumping device, this does not constitute any limitation, that is, the present invention is applicable widely to conventional pneumatically driven type pumps.

In some particular type of a pneumatically driven type pump, moreover, the branch line may be provided only with respect to any one of the positive pressure line 9 and negative pressure line 11.

Figure 9:
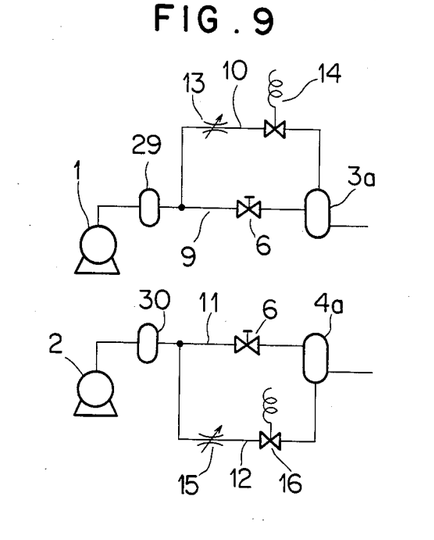
FIG. 9 is a partially omitted block diagram showing another embodiment.

Further, instead of connecting the branch lines 10 and 12 to the driving pressure outlet 7, the outlets of the valves 14 and 16 mounted respectively in the branch lines 10 and 12 may be connected to the positive pressure tank 3a and negative pressure tank 4a, respectively, as shown in FIG. 9. The branch lines may be connected to any point if only the connection is between the pressure reducing valve 6 and the pneumatically driven type pump 8, whereby it is made possible to compensate for the delay in response of the pressure reducing valve 6.

Instead of the electromagnetic change-over valve 5, solenoid valves may be disposed respectively on the output sides of the positive and negative pressure tanks 3a and 4a so as to be opened alternately with each other.

According to the present invention, as set forth hereinabove, a branch line which branches from between a pressure regulating valve (reducing valve) mounted on the inlet side of a positive pressure tank and a high pressure source (compressor) and is connected to between the pressure regulating valve and a pneumatically driven type pump, and/or a branch line which branches from between a pressure regulating valve (reducing valve) mounted on the inlet side of a negative pressure tank and a negative pressure source (vacuum pump) and is connected to between the pressure relulating valve and the pneumatically driven pump, are (is) provided, and when a positive pressure from the positive pressure tank or a negative pressure from the negative pressure tank is exerted on the pump, a positive pressure higher than the said positive pressure or a negative pressure lower than the said negative pressure is allowed to act for a short time in synchronism therewith directly from the branch line. Consequently, even without setting the capacity of the positive pressure tank and that of the negative pressure tank sufficiently large in comparison with the capacity of the pneumatically driven type pump, the pump can be operated as per the rating by supplying predetermined pressures thereto. As a result, it becomes possible to reduce the capacity of the positive pressure tank and that of the negative pressure tank and hence attain reduction in size of the entire system. Moreover, even if the driving pressure outlet and the pneumatically driven type pump are connected through a long flexible hose of a small diameter, it is possible to eliminate the influence of the intratube resistance, etc.

Figure 11:
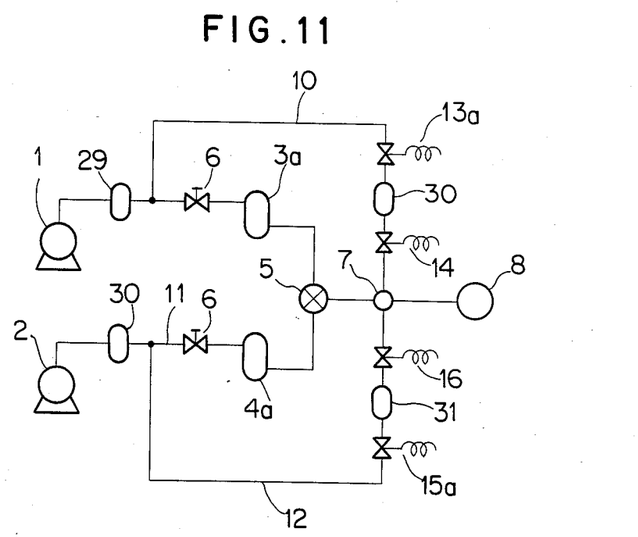
FIG. 11 is a block diagram showing an embodiment of the present invention.

Referring now to FIG. 11, there is shown another embodiment of the driving system of the present invention, in which the portions common to FIGS. 1, 5 and 9 are indicted at the same reference numerals. Explanation of such common portions will be omitted.

In this embodiment, a sub-positive pressure tank 30 with a capacity smaller than that of a positive pressure tank 3a is mounted in a branch 10 which brances from between a pressure reducing valve 6 provided on the inlet side of the positive pressure tank 3a and a compressor 1 and which directly interconnects the compressor 1 and a driving pressure outlet 7, while a sub-negative tank pressure 31 with a capacity smaller than that of negative pressure tank 4a is mounted in a branch line 12, which branches from between a pressure reducing valve 6 provided on the inlet side of the negative pressure tank 4a and a vacuum pump 2 and which directly interconnects the vacuum pump 2 and the driving pressure outlet 7. The interior of the sub-positive pressure tank 30 is pressurized at a level higher than the pressure in the positive pressure tank 3a, while the interior of the sub-negative pressure tank 31 is reduced in pressure to a level lower than the pressure in the negative pressure tank 4a.

Solenoid valves 14 and 13a are provided respectively on the outlet side (the driving pressure outlet 7 side) and inlet side (the compressor 1 side) of the sub-positive pressure tank 30, while solenoid valves 16 and 15a are provided respectively on the outlet side (the driving pressure outlet 7 side) and the inlet side (vacuum pump 2 side) of the sub-negative pressure tank 31.

Figure 12:
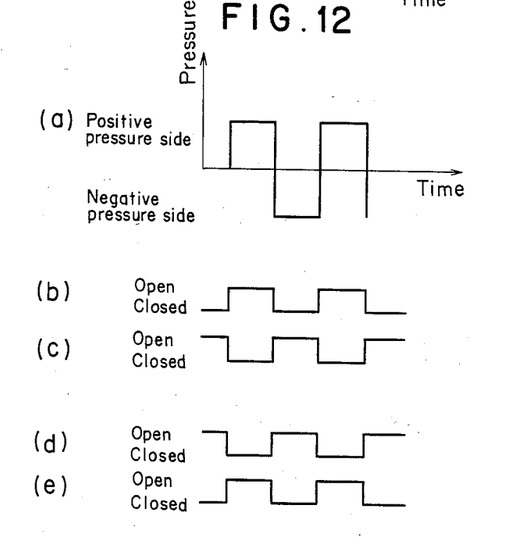

The solenoid valves 13a, 14, 15a, and 16 are each operated in synchronism with an electromagnetic change-over valve 5 by means of a control unit (not shown). FIGS. 12 (a)–(e) are timing charts of the electromagnetic changeover valve 5 and the solenoid valves 13a, 14, 15a and 16. According to those figures, when the electromagnetic changeover valve 5 switches to the positive pressure tank 3a side, the solenoid valves 14 and 15a open and the solenoid valves 13a and 16 close for a period of time corresponding thereto. On the other hand, when the valve 5 switches to the negative pressure tank side, the solenoid valves 16 and 13a open and the solenoid valves 14 and 15a close for a period of time corresponding thereto.

Thus, when the electromagnetic change-over valve 5 switches to the positive pressure tank side and pressurized gas acts on the pneumatically driven type pump 8 through the driving pressure outlet 7 from the positive pressure tank 3a, the pressurized gas in the sub-positive pressure tank 30 also acts thereon in synchronism therewith. On the other hand, when the electromagnetic change-over valve 5 switches to the negative pressure tank side and a suction of gas is effected from the pump 8 through the driving pressure outlet 7 by the negative pressure tank 4a, the sub-negative pressure tank 31 also sucks in the gas in synchronism.

Therefore, even if a pressure drop occurs in the positive pressure tank 3a, it is compensated for at the driving pressure outlet 7 and the pneumatically driven type pump 8 by the pressurized gas fed from the sub-positive pressure tank 30 and does not affect the pump.

Moreover, even if the pressure in the negative pressure tank 4a increases, this increase of pressure if compensated for at the driving pressure outlet 7 and the pump 8 by the suction of gas in the sub-negative pressure tank 31 and does not affect the pump.

Figure 13:
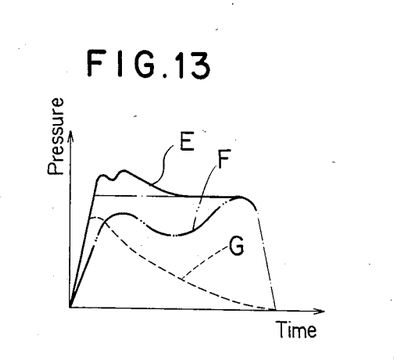
FIGS. 13 and 14 are pressure waveform diagrams obtained in the use of the driving system of the present invention.
Figure 14:
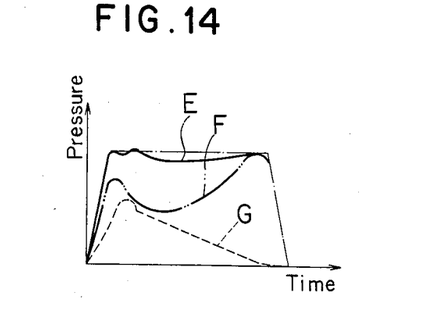

FIGS. 13 and 14 show pressure waveforms at the driving pressure outlet 7 and the pump 8 during supply of pressurized gas. According to these figures, with only the positive pressure tank 3a, a predetermined pressure is not reached until response of the pressure reducing valve 6 due to the influence of pressure drop as shown in the alternate long and two short dashes line F, but if the sub-positive pressure tank 30 is added, the pressurized gas (see the dotted line G) from the sub-positive pressure tank 30 makes a pressure compensation until response of the pressure reducing valve 6, so that the pressure waveform at the driving pressure outlet 7 and the pneumatically driven type pump 8 approaches an ideal waveform B as shown in the solid line E. The alternate long and two short dashes line F in FIG. 13 corresponds to the solid line A shown in FIG. 2, and the like line F in FIG. 14 corresponds to the solid line shown in FIG. 3.

Thus, in this embodiment, the sub-positive pressure tank 30 and the sub-negative pressure tank 31 perform pressure compensation not only at the beginning of pressurized air and the beginning of gas suction but also until response of the pressure reducing valve 6. Consequently, even if the capacity of the positive pressure tank 3a and that of the negative pressure tank 4a are set small, the pump 8 can be operated as per the rating.

The capacity and pressure of the sub-positive pressure tank 30 are set, for example, as follows.

It is here assumed that the capacity and pressure of the positive pressure tank 3a are B[l] and Y [atm], respectively, the capacity and pressure of the sub-positive pressure tank 30 are C[l] and X[atm], respectively, the total capacity of the pneumatically driven type pump 8 and the flow path (tube) is A[l] and the pressure(negative pressure) before action of positive pressure is Z[atm].

When the electromagnetic change-over valve 5 and the solenoid valve 14 open, an instantaneous pressure W of the tanks 3a and 30 and the load (the pneumatically driven type pump 8 and the flow path) is as shown by the following equation, assuming that air has not been replenished yet from the compressor 1 to the positive pressure tank 3a through the pressure reducing valve 6:

$$W = \frac{(B \times Y) + (A \times Z) + (C \times X)}{A + B + C} \text{ (atm)} \quad 1$$

For W=Y, the outflow from the positive pressure tank 3a may be assumed equal to be 0; in other words, this outflow may be compensated for by the sub-positive pressure tank 11.

Thus, $A(Y-Z)=C(X-Y)$, but in the case of $X=Y$, the right side becomes zero and an equality is reached when the B in the equation (1) becomes B+C, thus exhibiting no effect.

Therefore, the capacity and pressure of the sub-positive pressure tank 11 may be set so as to satisfy the following relationships:

$$X > Y \quad (2)$$

$$A(Y-Z) \geq C(X-Y) \quad (3)$$

In this case, it is preferable that the following condition be satisfied:

$$A(Y-Z) = KC(X-Y)$$

$$K: 1 \sim 0.01$$

For example, when A=0.2 [l], B=1.0 [l], Z=0.7 [atm] and Y=1.3 [atm], the value W=1.3 [atm] may be obtanied by setting C and X at 0.2 [l] and 1.9 [atm], respectively, or at 0.1 [l] and 2.5 [atm], respectively.

Thus, the capacity of the sub-positive pressure tank 11 can be set at a value about one-fifth to one-tenth of the capacity of the positive pressure tank 3a, and if the pressure of the sub-positive pressure tank 11 is set at a level not lower than 1.5 times that of the positive pressure tank 3a, it will be effective.

Figure 16:
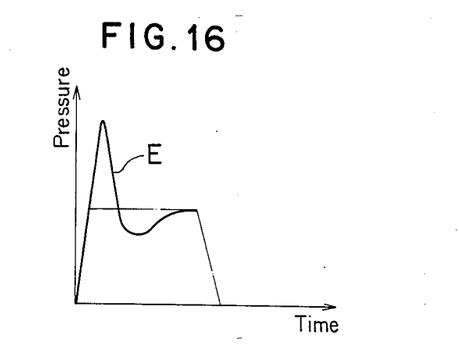
FIG. 16 is a pressure waveform diagram obtained when a sub-positive pressure tank is excessively pressurized.

If the pressure of the sub-positive pressure tank 30 is below 1.5 times that of the positive pressure tank 3a, the tank capacity must be made large, which is less effective due to the influence of the intratube resistance. But, if it is more than 10 times, the pressure waveform becomes like the one shown in FIG. 16, thus causing a problem. Therefore, it is preferable that the pressure of the sub-positive pressure tank 30 be set at a value in the range of 1.5 to 10 times the pressure of the positive pressure tank 3a.

The capacity and pressure of the sub-negative pressure tank 13 are also set in the same way. In this case, their values may be set so as to satisfy the following relationships, assuming that the capacity and pressure of the subnegative pressure tank 31 are C' [l] and X' [atm] respectively, the capacity and pressure of the negative pressure tank 4a are B' [l] and Y' [atm] respectively and the positive pressure of the pneumatically driven type pump before application of negative pressure is Z' [atm]:

$$X' < Y \quad (4)$$

$$A'(Y-Z) \leq C'(X'-Y) \quad (5)$$

When A=0.2 [l], B=1.0 [l], Y'=0.7 [atm], Z'=1.3 [atm] and X'=0.2 [atm], C' may be set as C'≦0.24 [l].

In the case where the sub-positive pressure tank 30 and the sub-negative pressure tank 31 are not used, the foregoing equation 1 becomes as follows:

$$W = \frac{(B \times Y) + (A \times Z)}{A + B}$$

In order for W to approach 1.3 [atm], assuming that A=0.2 [l], Z=0.7 [atm] and Y=1.3 [atm], the capacity the positive pressure tank 3a must be set at approximately 10 [l].

That is, the total capacity (1.2~1.1 [l]) of the positive pressure tank 3a and the sub-positive pressure tank 30 can be set at a fairly small value as compared with the capacity (about 10 [l]) of the positive pressure tank 3 shown in FIG. 1. The total capacity of the negative pressure tank 4 and the sub-negative pressure tank 13 can also be set at a fairly small value as compared with the capacity of the negative pressure tank 4 shown in the same figure.

Operation of the above embodiment will be described below.

The interior of the positive pressure tank 3a is maintained at a predetermined positive pressure by the compressor 1 and the interior of the negative pressure tank 4a is maintained at a predetermined negative pressure by the vacuum pump 2. When the electromagnetic change-over valve 5 switches to the positive pressure tank 3a side, pressurized gas is fed from the port 20 into the housing outer case 21 through the change-over valve 5 and the driving pressure outlet 7. At this time, the solenoid valve 14 opens in synchronism with the change-over valve 5 and the gas in the sub-positive pressure tank 30 pressurized higher than the pressure in the positive pressure tank 3a is fed into the housing outer case 21 from the port 20 through the solenoid valve 14 and the driving pressure outlet 7. Therefore, even if a pressure drop occurs in the positive pressure tank 3a until response of the pressure reducing valve 6, it does not affect at all the pressure waveform in the housing outer case 21. Consequently, the interior of the housing outer case 21 is pressurized to a predetermined level without delay in rise, whereby the blood in the blood chamber 22 is forced out from the blood discharging conduit 25 through the check valve 27. While the solenoid valve 14 is open, the solenoid valve 17 is also open and the sub-negative pressure tank 31 is reduced in pressure to a lower level than the negative pressure tank 4a by means of the vacuum pump 2, thus making preparations for the next operation. When the electromagnetic changeover valve 5 switches to the negative pressure tank 4a side, the solenoid valve 17 closes.

Then, when the change-over valve 5 swithces to the negative pressure tank 4a side, the gas in the housing outer case 21 is sucked into the negative pressure tank 4a through the port 21, driving pressure outlet 7 and change-over vlave 5 and discharged from the tank 4a to the exterior through the pressure reducing valve 6 by means of the vacuum pump 6. At this time, the solenoid valve 16 opens and the sub-negative pressure tank 31 also sucks in the gas from the interior of the housing outer case 13. Therefore, even if the pressure in the negative pressure tank 4a increases until response of the reducing valve 6, it does not affect at all the pressure waveform in the housing oùter case 21. Therefore, the interior of the housing outer case 21 is reduced in pressure to a predetermined level without delay in fall, whereby the check valve 26 is opened (while the check valve 27 is closed) and the blood is introduced from the blood introducing conduit 24 into the blood chamber 22. While the solenoid valve 16 is open, the solenoid valve 13a is also kept open and pressurized gas is fed from the compressor 1 into the sub-positive pressure tank 30, which is held at a higher pressure than the interior of the positive pressure tank 3a, thus making preparations for the next operation. When the electromagnetic change-over valve 5 switches to the positive pressure tank 3a side, the solenoid valve 13a closes.

Consequently, the blood pumping device can be operated as per the rating and the blood curve exhibited by the blood pumping device can be made as approximate as possible to that of a natural heart.

Although in the above embodiment the driving system of the present invention was applied to the blood pumping device, this does not constitute any limitation, that is, the present invention is applicable widely to conventional pneumatically driven type pumps.

In some particular pneumatically driven type pump, there may be used any one of the sub-positive pressure tank 30 and the sub-negative pressure tank 31.

Figure 15:
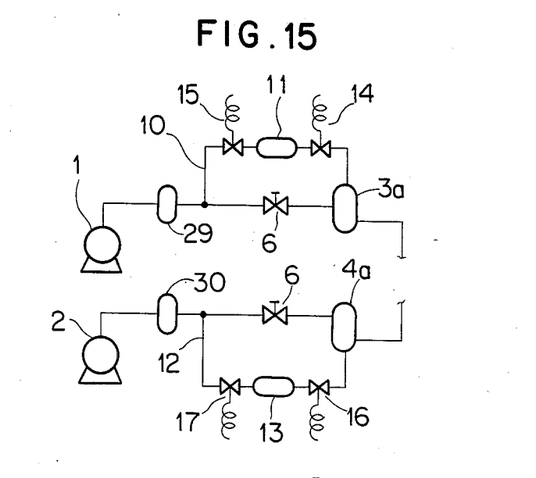
FIG. 15 is a partially omitted block diagram showing another embodiment.

Moreover, as shown in FIG. 15, the outlet portions of the sub-positive pressure tank 30 and sub-negative pressure tank 31 (outlet portions of the solenoid valves 14 and 16) may be connected to the positive pressure tank 3a and negative pressure tank 4a instead of being connected to the driving pressure outlet 7. Also in this case there can be attained the same function and effect.

Further, instead of the solenoid valve 5, solenoid valves may be disposed respectively on the outlet sides of the positive pressure tank 3a and the negative pressure tank 4a so as to be opened alternately with each other.

According to the present invention, as set forth hereinabove, a sub-positive pressure tank whose capacity is smaller than that of a positive pressure tank and which is connected to a high pressure source (compressor) and pressurized to a level higher than the pressure of the positive pressure tank, and/or a sub-negative pressure tank whose capacity is smaller than that of a negative pressure tank and which is connected to a negative pressure source (vacuum pump) and reduced in pressure to a lower level than the pressure of the negative pressure tank, are (is) provided, and when a positive pressure or negative pressure is exerted on a pneumatically driven type pump from the positive pressure tank or negative pressure tank, the positive pressure in the sub-positive pressure tank or negative pressure in the sub-negative pressure tank is exerted thereon in synchronism therewith. Therefore, even without setting the capacity of the positive pressure tank and that of the negative pressure tank sufficiently large as compared with the capacity of the pneumatically driven pump, the pump can be operated as per the rating by supplying predetermined constant pressures thereto. Consequently, the capacity of the positive pressure tank and that of the negative pressure tank can be reduced, that is, the reduction in size of the entire system can be attained.

Further, since there are used the sub-positive pressure tank and the sub-negative pressure tank, a pressure drop and an increase of pressure in the positive pressure tank and the negative pressure tank can be compensated for not only at the beginning of application of positive and negative pressures but also until the pressure reducing valves provided on the inlet sides of the positive pressure tank and the negative pressure tank compensate for such pressure drop and increase. Consequently, by suitably setting the tank capacity and pressure, it is made possible to make the pressure waveform in the pneumatically driven type pump approximate to the ideal waveform.

Further, even if the driving pressure outlet and the pneumatically driven type pump are interconnected through a long flexible hose of a small diameter, it is possible to compensate for the influence of intratube resistance and tube deformation.

EXAMPLE I

A example of the present invention will be described below.

Using the driving system shown in FIG. 5, a blood pump having a capacity of 200 cc. as a total capacity of pump and tube was driven and the pressure waveform in the housing outer case was measured by a pressure transducer. The pressure waveform obtained is as shown with solid line in FIG. 7. At this time, the capacity and pressure of the positive pressure tank 3a were 2 l and 0.26 kg/cm$^2$, respectively, and the capacity and pressure of the negative pressure tank 4a were 2 l and −0.03 kg/cm$^2$ respectively. The opening time of the solenoid valves 14 and 16 was 80 msec, the positive pressure from the branch line 10 was 1 kg/cm$^2$ and the negative pressure from the branch line 12 was −0.799 kg/cm$^2$.

EXAMPLE II

Another example of the present invention will be described below.

Using the driving system shown in FIG. 4, a blood pump having a capacity of 200 cc. as a total capacity of pump and tube was driven and the pressure waveform in the housing outer case was measured by a pressure transducer. The pressure waveform obtained is approximately as shown with solid line in FIG. 6.

The capacities and pressures of the tanks 3a, 4a, 11 and 13 and the operation times of the solenoid valves 13a, 14, 15a, 16 were as follows:

Tank 3a: 2 [l], 0.26 kg/cm$^2$
Tank 4a: 2 [l], −0.03 kg/cm$^2$
Tank 11: 0.07 [l], 1 kg/cm$^2$
Tank 13: 0.07 [l], −0.79 kg/cm$^2$ (−600 mmHg)
Solenoid valve 5: 20 msec (on the positive pressure tank 3a side) 20 msec (on the negative pressure tank 4a side)
Solenoid valves 14, 16: 10 msec
Solenoid valves 15, 17: 30 msec.

COMPARATIVE EXAMPLE

Figure 10:
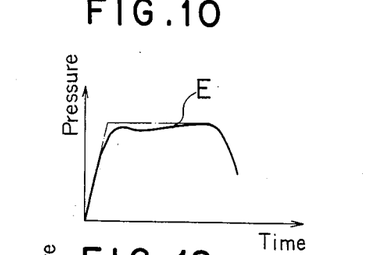
FIG. 10 is a waveform diagram obtained in the use of the driving system of FIG. 1.

As a comparative example, there was used the driving system shown in FIG. 1. In this case, the following tank capacities were required for obtaining the pressure waveform shown with solid line in FIG. 10:

Tank 3: 10 l
Tank 4: 10 l

Thus, in the present invention, the total tank capacity can be reduced to approximately one-fifth of that of the driving system shown in FIG. 1.

What is claimed is:

1. A driving method for a blood pumping device which is driven by applying to a driving portion of a blood pumping device positive and negative pressures alternatively from a positive pressure tank connected through a pressure regulating valve to a high pressure source and a negative pressure tank connected through a pressure regulating valve to a negative pressure source, comprising when the positive pressure of both the positive and negative pressures are exerted on the above driving portion, compensating pressures for pressure drop and rise in the positive and negative pressure tanks are exerted thereon in synchronism therewith without going through the pressure regulating valves.

2. A system for driving a pump which is of a type pneumatically driven by being alternatively applied with positive and negative pressures comprising (a) a positive pressure source for producing a high pressure;
(b) a positive pressure tank for accumulating the positive pressure generated by the positive pressure source; said positive pressure tank being connected with the positive pressure source;
(c) a positive pressure regulating valve between the positive pressure source and the positive pressure tank for regulating the pressure from the positive pressure source into a given pressure;
(d) a negative pressure source for producing a negative pressure;
(e) a negative pressure tank for accumulating the negative pressure generated by the negative pressure source; said negative pressure tank being connected with the negative pressure source;

(f) a negative pressure regulating valve between the negative pressure source and the negative pressure tank for regulating the pressure from the negative pressure source into a given pressure;

(g) a change-over valve for alternatively connecting the positive and negative pressure tanks with a port which is to be connected with the pump;

(h) a positive pressure branch having an inlet between the positive pressure source and the positive pressure regulator and an outlet between the positive pressure regulator and the pump for applying a pressure higher than that from the positive tank when the latter is applied upon the pump; and (i) a negative pressure branch having an inlet between the nagative pressure source and the negative pressure regulator and an outlet between the negative pressure regulator and the pump for applying a pressure lower than that from the negative pressure tank when the latter is applied upon the pump.

3. The system as defined in claim 2 in which the outlets of the positive and negative pressure branches are connected to the outlet of the system.

4. The system as defined in claim 2 in which the outlets of the positive and negative pressure branches are connected to the positive and negative pressure tanks respectively.

5. The system as defined in claim 2 in which the positive and negative pressure branches have positive and negative sub-pressure tanks respectively which contain pressures higher and lower than that in the positive and negative tanks respectively.

6. The system as defined in claim 5 in which the outlets of the positive and negative pressure branches are connected to the outlet of the system.

7. The system as defined in claim 5 in which the outlets of the positive and negative pressure branches are connected to the positive and negative pressure tanks respectively of the system.

8. The system as defined in any one of claims 2 to 7 in which each of the branches has valves for pressure regulation and the timing control of the pressure application.

* * * * *